United States Patent
Kalensky

(10) Patent No.: US 11,185,659 B2
(45) Date of Patent: Nov. 30, 2021

(54) SYSTEM AND METHOD FOR A DIGITALLY-INTERACTIVE PLUSH BODY THERAPEUTIC APPARATUS

(71) Applicant: Fiona Eileen Kalensky, Chicago, IL (US)

(72) Inventor: Fiona Eileen Kalensky, Chicago, IL (US)

( * ) Notice: Subject to any disclaimer, the term of this patent is extended or adjusted under 35 U.S.C. 154(b) by 389 days.

(21) Appl. No.: 16/253,881

(22) Filed: Jan. 22, 2019

(65) Prior Publication Data

US 2019/0224444 A1    Jul. 25, 2019

Related U.S. Application Data

(60) Provisional application No. 62/620,331, filed on Jan. 22, 2018.

(51) Int. Cl.
  *A61M 21/02*    (2006.01)
  *A63H 30/02*    (2006.01)
  (Continued)

(52) U.S. Cl.
  CPC .......... *A61M 21/02* (2013.01); *A61B 5/4088* (2013.01); *A63H 3/001* (2013.01); *A63H 3/003* (2013.01); *A63H 3/28* (2013.01); *A63H 13/02* (2013.01); *A63H 30/02* (2013.01); *A61B 5/16* (2013.01); *A61B 5/6887* (2013.01); *A61M 2021/0022* (2013.01); *A61M 2021/0027* (2013.01); *A63H 2200/00* (2013.01)

(58) Field of Classification Search
  CPC .......... A61M 21/02; A61M 2021/0027; A61M 2021/0022; A61M 21/00; A61M 2021/0061; A61M 2021/0088
  See application file for complete search history.

(56) References Cited

U.S. PATENT DOCUMENTS

| | | |
|---|---|---|
| 2,774,184 A | 12/1956 | Albert et al. |
| 4,075,782 A | 2/1978 | Neuschatz |

(Continued)

OTHER PUBLICATIONS

Roger, "Social Commitment Robots and Dementia", Canadian Journal on Aging 31 (1), (2012) (87-94), doi: 10.2017/S0714980811000663.

(Continued)

*Primary Examiner* — Samuel G Gilbert

(74) *Attorney, Agent, or Firm* — Alpine Patents LLC; Brian Van Osdol

(57) ABSTRACT

A system and method for a therapeutic apparatus that includes an external casing of a first therapeutic apparatus, wherein the external casing comprises of a plush body, the external casing comprising at least one compartment; a therapeutic module system that comprises of a set of interaction devices and a wireless communication system, wherein the therapeutic module system may be removably oriented into the at least one compartment; the set of interaction devices comprising of: sensing inputs that comprise of a auditory sensing system, a haptic sensing system, an olfaction sensing system, and other biosensing systems, and output systems that comprise of at least an auditory feedback and haptic feedback systems; and a processing system that comprises configuration to assess the state of a subject through the sensing inputs and control the output systems in response to the sensing inputs.

24 Claims, 5 Drawing Sheets

(51) Int. Cl.
*A61B 5/00* (2006.01)
*A63H 3/00* (2006.01)
*A63H 13/02* (2006.01)
*A63H 3/28* (2006.01)
*A61M 21/00* (2006.01)
*A61B 5/16* (2006.01)

(56) References Cited

U.S. PATENT DOCUMENTS

| | | |
|---|---|---|
| 4,601,668 A | 7/1986 | Sirota |
| 4,718,876 A * | 1/1988 | Lee ................. A61M 21/00 446/295 |
| 4,737,131 A | 4/1988 | Sirota |
| 4,740,186 A | 4/1988 | Sirota |
| 4,917,607 A | 4/1990 | Hoose |
| 5,037,302 A | 8/1991 | Sirota |
| 5,094,621 A | 3/1992 | Friedel |
| 5,842,870 A | 12/1998 | Cramer |
| 6,004,136 A | 12/1999 | Ehrenpreis |
| 6,514,117 B1 | 2/2003 | Hampton et al. |
| 7,547,278 B2 | 6/2009 | Miyazaki et al. |
| 8,313,330 B2 | 11/2012 | Maspoli et al. |
| 8,909,370 B2 | 12/2014 | Stiehl et al. |
| 9,079,113 B2 * | 7/2015 | Wong ................... A63H 3/001 |
| 9,251,713 B1 | 2/2016 | Giovanniello et al. |
| 9,345,433 B1 | 5/2016 | Shinozuka et al. |
| 9,390,626 B1 | 7/2016 | Horowitz et al. |
| 9,747,816 B2 | 8/2017 | Chenoweth |
| 2004/0161732 A1 | 8/2004 | Stump et al. |
| 2004/0197764 A1 | 10/2004 | Stump et al. |
| 2005/0101844 A1 * | 5/2005 | Duckert ............... A61B 5/0002 600/300 |
| 2007/0099538 A1 | 5/2007 | Friedland et al. |
| 2008/0214089 A1 | 9/2008 | Vermac et al. |
| 2009/0055019 A1 * | 2/2009 | Stiehl ..................... B25J 9/1656 700/249 |
| 2009/0156089 A1 | 6/2009 | Hoard et al. |
| 2009/0198145 A1 | 8/2009 | Chow |
| 2010/0145514 A1 | 6/2010 | Kim et al. |
| 2012/0026625 A1 | 2/2012 | Thurn et al. |
| 2013/0053656 A1 | 2/2013 | Mollicone et al. |
| 2015/0065989 A1 | 3/2015 | Moberg et al. |
| 2015/0112121 A1 | 4/2015 | Eyrun |
| 2016/0029962 A1 | 2/2016 | Hyde et al. |
| 2016/0029963 A1 | 2/2016 | Hyde et al. |
| 2016/0088818 A1 | 3/2016 | Thorne |
| 2016/0155310 A1 | 6/2016 | Joao et al. |
| 2016/0157074 A1 | 6/2016 | Joao et al. |
| 2016/0227740 A1 | 8/2016 | Nunn |
| 2016/0324478 A1 | 11/2016 | Goldstein |
| 2017/0025043 A1 | 1/2017 | Chenoweth |
| 2017/0087726 A1 | 3/2017 | Gnana et al. |
| 2019/0110471 A1 * | 4/2019 | Kim ........................ B32B 5/02 |

OTHER PUBLICATIONS

V. Bernabei, "Animal-assisted interventions for elderly patients affected by dementia or psychiatric disorders: A review", Journal of Psychiatric Research, 47 (2013) (762-773) www.elsevier.com/locate/psychires, Accepted Dec. 27, 2012.

* cited by examiner

Collecting patient interaction signals S110

Interpreting the interaction signals S120

Controlling the output of the simulated living apparatus S130

FIGURE 3

Preparing a pad bath S210

Running the fur coating through the pad bath S220

Drying the fur coating S230

FIGURE 4

Heating the silver chloride S310

Preparing an antimicrobial solution S320

Creating an antimicrobial pad bath solution S330

Treating the fur coating S340

Curing the fur coating S350

FIGURE 5

SYSTEM AND METHOD FOR A DIGITALLY-INTERACTIVE PLUSH BODY THERAPEUTIC APPARATUS

CROSS-REFERENCE TO RELATED APPLICATIONS

This application claims the benefit of U.S. Provisional Application No. 62/620,331, filed on 22 Jan. 2018, which is incorporated in its entirety by this reference.

TECHNICAL FIELD

This invention relates generally to the field of therapeutic aid devices and more specifically to a new and useful system and method for a digitally-interactive plush body therapeutic apparatus.

BACKGROUND

Dementia is a progressive and chronic brain condition that causes difficulty with memory, thinking and behavior. The most common form of dementia, Alzheimer's Disease, currently affects 5.7 million people in the US and it is projected to increase to 14 million by 2050. Worldwide the number of persons with dementia is projected today to be 47 million. Over the past decades, scientists and researchers have explored dementia treatment through cognitive stimulation, drug interference, and other methods. Animal-assisted therapy has been explored as a treatment on patients with dementia and it has been shown to help improve patients' apathetic state, decrease their irritability and depression scale, and/or boost their social interaction and participation in long-term care. However, there are many reasons why pets cannot be used in many cases. As one problem, pets can be demanding and may increase the stress of patients and do more harm than good. As another problem when dealing with care facilities, a large number of pets for patients may not be operationally feasible, especially when a facility is providing care for a large population. As another problem, pets may not be suitable for patients with allergies, with compromised immune systems, particular physical disabilities, or other issues. Thus, there is a need in the therapeutic aid field to create a new and useful system and method for a digitally-interactive plush body therapeutic apparatus. This invention provides such a new and useful system and method.

BRIEF DESCRIPTION OF THE FIGURES

FIG. 3 is a flowchart representation of a method for a preferred embodiment;

FIG. 4 is a flowchart representation of a method for an antimicrobial plush body fur treatment for a therapeutic apparatus of a preferred embodiment; and FIG. 5 is a flowchart representation of a method for alternate antimicrobial plush body fur treatment for a therapeutic apparatus of a preferred embodiment.

DESCRIPTION OF THE EMBODIMENTS

Figure 1:
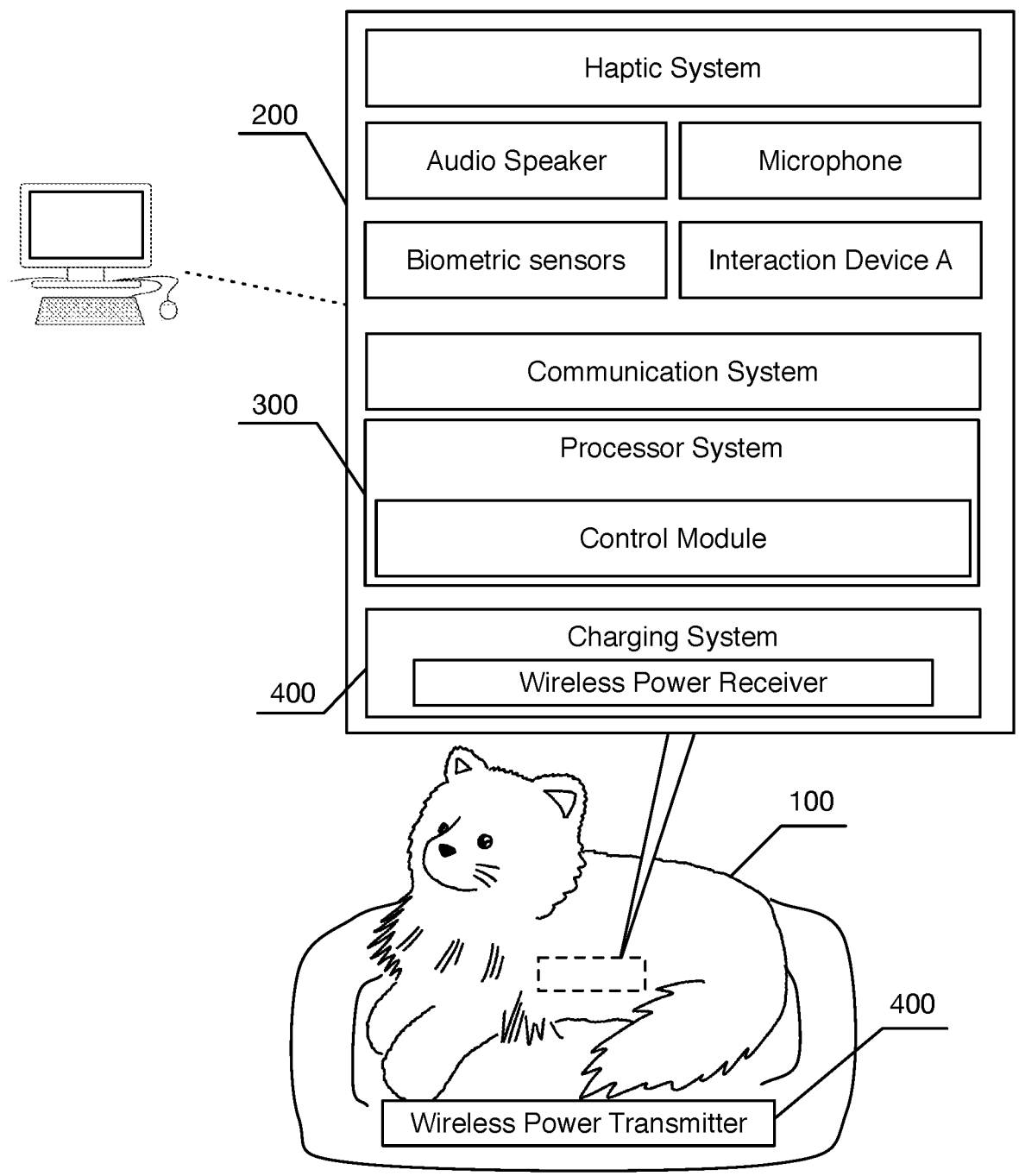
FIGS. 1 and 2 are schematic representations of variations of system of a preferred embodiment.

The following description of the embodiments of the invention is not intended to limit the invention to these embodiments but rather to enable a person skilled in the art to make and use this invention.

1. Overview

A system and method for a robotic and digitally-interactive therapeutic apparatus functions to provide care for a subject or user through various forms of interactions that are responsive to the state of the subject and environment and that replicate therapeutic aspects of a therapy animal. The system and method preferably operate and are designed to artificially simulate some of the features of a companion animal (i.e., therapy animal). The system and method can include: a stuffed plush body casing with sensor components to monitor the subject; output components that simulate animal behavior and provide feedback interaction with the subject; and additional processing, control, communication, and power components. The system and method preferably incorporates modular components enabling the simple customization of the therapeutic apparatus for user treatment and as well as variations of potential environmental factors (e.g. a more lightweight version for travel).

The user is preferably a human subject (although the system may alternatively be used by other animals) and may be an individual suffering from dementia or additionally and/or alternatively be suffering from any other mental and/or physical conditions. The system and method may provide therapeutic aid to improve the emotional health of the subject and/or provide caregivers with user data. Hence forth, the subject is primarily described as the patient or the user but may refer to any suitable user or group of users. The system and method may be used by a subject living in a care facility, palliative care facility, rehabilitative facility, hospice facility or in a home care setting. Additionally, the system and method may include functionality to coordinate operation of multiple therapeutic apparatuses. Alternatively, subjects in a care facility may each use a therapeutic apparatus that independently interacts with the subject.

In particular, the system and method simulates an animal, creature, or other form of a being. The system and method can enable responsive and dynamic interactions between the patient and system that can promote tactile interactions (e.g., petting, rocking, hugging, holding), physical movement (e.g., carrying and/or walking with the simulated being), auditory interactions, communication interactions, olfactory interactions, gustatory interactions, visual interactions, and/or other forms of interaction and stimulation.

The system and method may additionally observe trends and apply learning algorithms to the patient interactions and general patient behavior to better understand and provide therapeutic aid to the patient. The system and method may non-invasively monitor the behavior and reactions of the patient and over time improve simulated animal and patient interactions to improve both care and treatment of the patient.

The system and method are preferably designed to help provide potential therapeutic benefits to a patient. In some implementations, the system and method may alleviate stress and anxiety within a subject and potentially reduce loneliness. The system and method can additionally act as a platform for caregivers providing therapeutic treatment, monitoring interactions and patient vitals, and/or monitoring or administrating other aspects of care.

The system and method are preferably offered through an interactive aid device (herein primarily referred to as a therapeutic apparatus) that may be in the form of a lightweight and durable stuffed animal with an integrated therapeutic electronic module. In different implementations, the size and weight of the stuffed animal may change depending on the required and beneficial therapeutic components for a given patient. In one exemplary implementation, the system and method could be offered in the form of a stuffed pet like a dog, cat, or any suitable animal. The plush body's form factor is preferably adaptable and can allow for a wider variety of appearances. A particular appearance may be customized or selected for a given subject. For example, the plush body may be formed as a particular breed of an animal (e.g., a dog breed common or owned when the subject was younger), which could be beneficial and comforting to a user due to its familiarity. The simulated animal may be a fur-covered and/or soft object or other suitable object in the shape and form of an animal or creature, which may function to promote the establishment of a cognitive relationship between the patient and the simulated being. The system and method may alternatively be used within other types of objects, like an artificial or imaginary animal or person, and may even be presented as purely therapeutic device without explicit imitation of a real-life object (e.g., an abstract-shaped therapeutic electronic module).

The system and method preferably provides a multi-sensory experience for the patient. In a preferred implementation, the system and method are able to detect tactile input through a haptic system such as a capacitive touch sensor. As the patient interacts with the therapeutic apparatus (e.g., petting, hugging, holding, rocking, etc.), the therapeutic apparatus may respond by generating various forms of therapeutic feedback such as haptic and auditory feedback. Haptic feedback can be in the form of soothing vibrations that simulate the purring of a live animal through a small actuator (e.g., a linear resonant actuator, a vibrational motor with eccentric mass, a piezo actuator). In one variation of auditory and haptic feedback, the therapeutic apparatus may generate and modulate simulated biological properties like a heartbeat or breathing, or sounds familiar to the patient, which can be used to calm the patient. Through the use of touch and proximity sensors, accelerometers, microphones, light sensors, and/or other device inputs, the system and method can assess the nature of a patient's behavior, and dynamically adjust the interactions in different operating modes to generate different therapeutic effects. In particular, the system and method can use various forms of biological sensing inputs to measure signals relating to body temperature, heart rate, respiration, and the like. The biological signals and other forms of detected input such as auditory cues (e.g., speech volume) and physical device interactions may be processed and assessed to determine when and how to provide feedback as well as the response to and effectiveness of feedback.

As one potential benefit, the system and method can be applied to the treatment of various types of subjects. As discussed, the system and method preferably provides therapeutic treatment in a similar manner as a real therapy animal, but through a device that can be more widely used, maintained and controlled. Unlike a real therapy animal, the interactive therapeutic apparatus requires minimal care. As such, the system and method can expand the number of cases in which such treatment can be applied and can provide data to the caregiver to assess the patient.

As a potential benefit over a real therapy animal, there is no additional cost to train each device as opposed to each individual therapy animal. A real therapy animal is also accompanied by real physical care (feeding, cleaning, etc.). A real therapy animal may also pose other complications such as triggering subject allergies, which the system and method can work to avoid. Additionally, the system and method enables caregivers to continuously monitor their patients, which can lead to improved patient care and increased data availability.

As another potential benefit, the system and method may provide a more economical offering, enabling the therapeutic apparatus to provide aid to multiple patients because of the affordability of the product. The system and method, in some implementations, may make use of a modular design approach to integration of the form factor and the digitally interactive electronic elements. For example, the system could employ a therapeutic module system that can be into a plush body external casing (which may be in the form of a stuffed animal). This modular approach can be a cost effective approach to manufacturing and assembly. A modular design approach can additionally facilitate offering a variety of form factors so that more options of stuffed animal bodies are available. In some implementations of the modular design approach, modular components can be selectively used in a given therapeutic apparatus, which may enable better focused care with reduced cost for a patient, by incorporating only relevant components customized for a specific patient.

As another potential benefit, the therapeutic electronic module can be integrated in a soft, comfortable form factor. While some implementations of the system and method may include internal rigid parts such as actuators, the therapeutic apparatus maintains a soft feel due to the form factor. The patients may pet, hug, cuddle, and occasionally fall asleep with the therapeutic apparatus, and so a comfortable soft form factor can aid in encouraging its use and patient ensure safety.

As a related potential benefit, the system and method can provide enhanced hygiene for the therapeutic apparatus intended for such direct physical interaction by the patient. The system and method may enable the use of antimicrobial fur. Additionally, the antimicrobial and sanitary outer plush body casing can be designed to still provide various textures useful in enabling different tactile sensations during interactions.

In addition to offering benefits to the treatment of a patient, the system and method may additionally provide potential benefits to caregivers such as attendants, medical staff, family members, and/or other suitable caregivers. The therapeutic apparatus can communicate with a caregiver through a remote monitoring system, which may enable a caregiver to monitor device usage and interactions, track patient vitals (heart rate, temperature, and respiration), adjust settings, or manage in other suitable ways. In some variations, the system and method may additionally include integration with home automation systems, digital personal assistant systems, home monitoring systems and the like. The system and method could enable coordination between the device and such automation systems allowing for continuous care monitoring.

2. System for a Therapeutic Apparatus

As shown in FIG. 1, a system of an a robotic and digitally-interactive therapeutic apparatus of a preferred embodiment includes an external casing 100, a therapeutic module system 200 that includes a set of interaction devices, a processing system 300 that processes inputs and controls outputs of the interaction devices, and a charging system 400. The set of interaction devices preferably provides a set of input/output subsystems comprising of different channels for reading interactions of the subject and creating an interaction with the subject. The processing system 300 preferably modulates output in coordination with sensed inputs (e.g., through the therapeutic module system 200) to promote various forms of interaction by a subject. For example, the therapeutic apparatus may make soothing sounds or haptic output during periods when the subject could benefit from a calming presence. The timing and properties of feedback like the soothing sounds or haptic output can be determined through detected user interaction and biological indicators. Forms of input that may be used by the therapeutic apparatus can include detected physical/haptic interactions with the apparatus, speech volume, body temperature, respiration pattern, heart rate, and the like. In some variations, the interaction devices can be selectively modular and may be added to or taken out of the therapeutic apparatus. The input/output devices of a therapeutic apparatus can include a microphone device, a speaker device, a haptic system, a biological monitoring system, a wireless communication system, and/or other suitable devices. The haptic system preferably includes haptic sensing and feedback systems, wherein the haptic sensing systems detect tactile interactions and the haptic feedback systems provide tactile output.

The system preferably functions as a therapeutic or an emotional aid device for one or more subjects. The therapeutic apparatus as described above is preferably digitally interactive and simulates a living being (real or imaginary). In some cases, the therapeutic apparatus may be alternatively described as a simulated living digital or smart companion and/or therapy animal. The system and its components may additionally be at least partially modular. For example, external casing 100 and the therapeutic module system 200 may be easily separable.

In some instances as described herein, the system includes multiple therapeutic apparatuses that are communicatively coupled through one or more control systems. The plurality of therapeutic apparatuses may be controlled in a coordinated fashion. This variation may be particularly applicable when used in a care facility where multiple subjects are individually using a therapeutic apparatus.

The external casing 100 of a preferred embodiment functions as the body of the therapeutic apparatus and preferably encases therapeutic modular system. The external casing 100 may encase additional components as desired. The external casing 100 is preferably a plush body (i.e., a soft doll body). The plush body in a preferred implementation is that of a stuffed animal (realistic or fantasy) with a form approximating that of an animal or character. In one implementation, the system could be offered through a variety of options of external casings 100. For example, the external casing could be offered as a poodle, a cairn terrier, a beagle, a pomeranian, and the like. A particular breed could be selected for a particular user based on past familiarity and history with a given breed. A stuffed animal can include various simulated body parts: like arms, legs, a tail, eyes, ears, a nose, and/or other suitable elements found in stuffed animals. Examples of stuffed animal forms include: teddy bear, dog, cat, giraffe, unicorn, dragon, and the like. In other preferred implementations, the plush body may have a humanoid form, such as boy doll, girl doll, prince/princess doll, farmer doll, and the like. The plush body may alternatively be of any suitable form. For example, one alternative implementation may have the plush body in the form of a pillow or a stuffed shape lacking animalistic/human features.

The plush body preferably includes filling material and a plush outer covering that encases the filling material. The filling material may be any suitable filling. In one variation, the plush body can include a localized section of weighted filling material such as weighted beads. The weighted filling material may promote proper orientation of the plush body during interactions and when the object is placed at rest in system 400 for charging. In one variation, localized weighting may be used to promote ease of wireless charging by promoting better alignment of wireless charging components. In one variation, the weighted filling material can be oriented within the form of the plush body in close proximity to wireless charging components such that the wireless charging components will be more stably positioned along the bottom surface when the plush body is set down. Preferably a charging mat or other charging system may be placed on a surface, which then charges the therapeutic module system 200. Other relative positioning of weighted material and/or wireless charging components may alternatively be used depending on charging station configuration.

The plush body outer covering functions as the surface exposed to the patients. The plush body outer covering is preferably a fur coating (e.g., artificial/synthetic fur) but could alternatively be any suitable type(s) of material(s) or texture, which provides beneficial stimulation to the patient. A suitable material preferably provides tactile stimulation that is generally characterized by possessing a texture across its surface. Synthetic fur would be one option, but various kinds of fabric, textile coatings, formed materials (e.g., coating of rubber/silicone filaments), and other alternatives could also be used. The fur coating may have multiple sub-regions with different fur properties. Varied fur properties can be used to offer different textures, which in some variations can provide beneficial stimulation for a patient. The selection and patterning of the plush body outer covering may be customized to facilitate cooling and management of thermodynamics of the therapeutic module system. For example, a portion of the external casing in proximity to a base portion of the therapeutic module system can be made of material and have filling that provides ventilation and heat transfer.

In some preferred variations, the outer plush body covering can include hygienically-enhanced fur. More generally, the plush body outer coating can be similarly enhanced (e.g., hygienically-enhanced fabric). Treatment to fur coatings described herein is one preferred implementation, but the treatments are not limited to only fur coatings. Hygienically-enhanced fur can enable the plush body to have antimicrobial properties that may improve bacterial protection. The hygienically-enhanced fur is preferably biocompatible and non-toxic. This may be beneficial to patients due to the close interaction between the patients and the therapeutic apparatus. In one variation, the outer plush body covering can include a short polyester and/or acrylic blend treated with an antimicrobial layer. The fur is preferably treated with the antimicrobial layer that bounds to the fabric of the fur. The synthetic fur may have other types of antimicrobial treatments such as those described herein. In another preferred implementation, the plush body may be treated with silver-nano material, ensuring antimicrobial properties.

The outer plush body covering may have other types of hygienically-enhanced material. The synthetic fur may have any desired non-toxic treatments as desired. Examples of hygienically-enhanced fur can include hypoallergenic and/or anti-fungal treated fur. In one preferred example, the synthetic fur is also treated with anti-fungal Zinc nanomaterials.

The external casing 100 may be made to be machine washable. In one variation, the external casing 100 is preferably separated from the therapeutic module system 200 and other components and then washed. In another variation, the other components within the external casing 100 are made water tight, for resilience, and the external casing 100 and internal components may be washed together.

The external casing 100 of the therapeutic apparatus preferably encases the therapeutic module system 200 and all interaction devices. The external casing 100 may have any type of compartment(s) necessary to contain the interaction devices (e.g. pockets, sleeves). A compartment is preferably a defined cavity. In one variation, the compartments are lined to establish separation from the filling. In one preferred variation, the therapeutic module system 200 is a substantially singular device that can be inserted within one compartment as shown in FIG. 1. In alternative variations, the therapeutic module system 200 may include multiple distinct modular interaction devices that can be inserted into a set of different compartments. For some instances, the therapeutic module system 200 or an interaction device of the therapeutic module system may be removably oriented in the compartment and in other instances the interaction device may be substantially fixed within a compartment or otherwise more permanently integrated into the plush body. For the plush body external casing 100, interaction device may be sewn in place, snapped in place, inserted within a pocket or sleeve, adhere in place, or incorporated in some other fashion.

Figure 2:
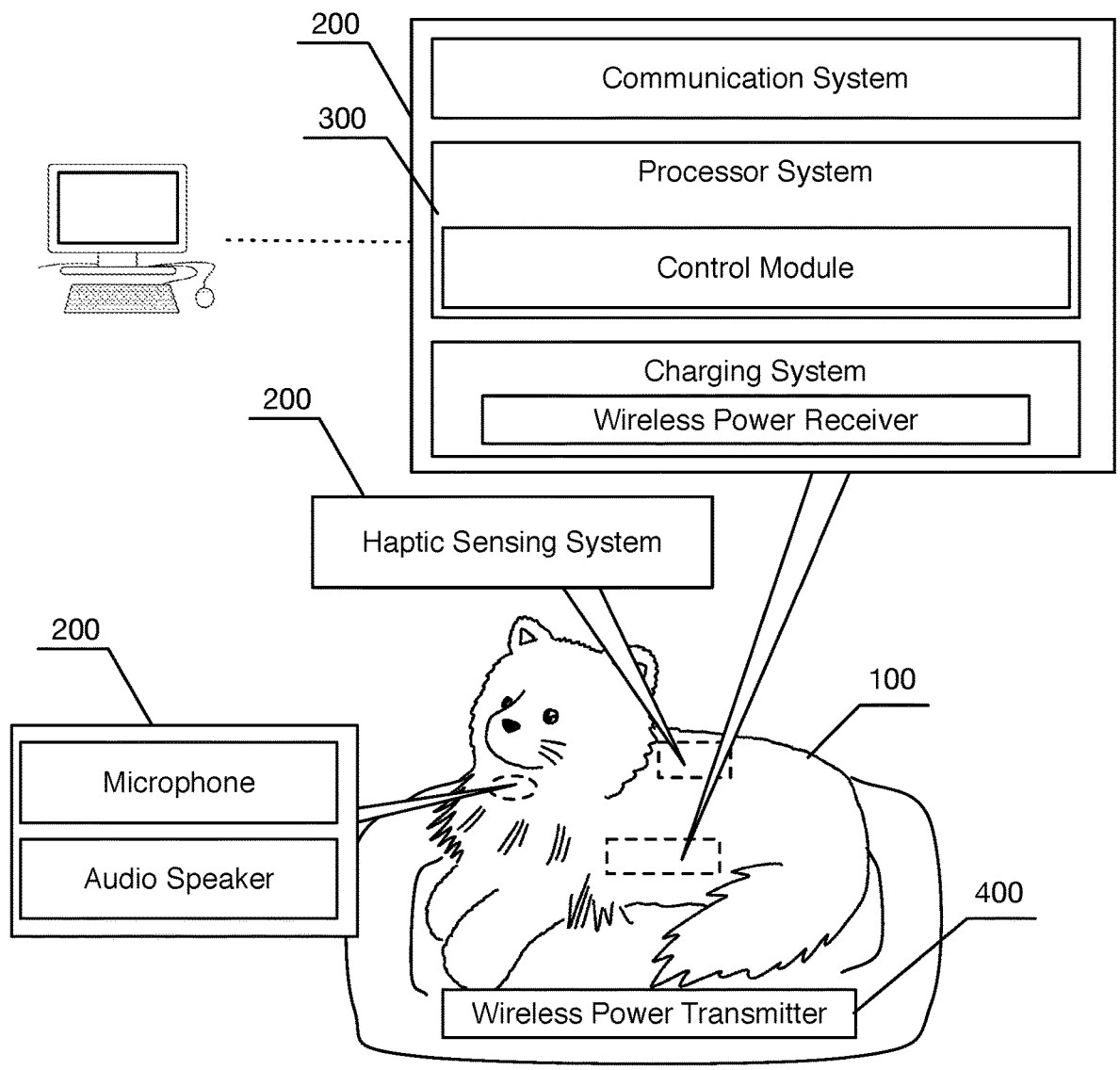

Dependent on the desired system utilization, different variations of external casings 100 may be implemented. In one preferred variation, the external casing 100 contains a single pocket for all internal components (e.g. a therapeutic module system 200 with all interaction devices) as shown in FIG. 1. Preferably the internal components may be placed or taken out as desired. In another preferred variation, the external casing 100 further has location specific "pockets" to encase specific interaction devices wherein different portions of the therapeutic module system 200 are oriented in distinct defined compartments as shown in FIG. 2. For example, a plush body cat external casing 100 may have pockets in each paw for the placement of haptic feedback systems (e.g. to enable the therapeutic apparatus to create a "purr"-effect while being held). Examples of other location specific compartments include: nose (e.g. breathing), mouth (e.g. sound output), head (e.g., haptic sensing system for detecting petting), body surface (e.g. sensors), and/or the like.

In one variation, the external casing 100 does not include integrated electronics, actuators, or aspects outside of the interaction devices. A fully external casing 100 may avoid discomfort introduced by integrated rigid systems. Alternatively, the system may include various electronic, or mechatronic elements, and/or sensors that are integrated within the external casing 100. For example, electronically controlled eyes, mouth, limbs, or tail could be integrated and designed to electronically couple to a therapeutic electronic module through a wired or wireless connection for power and/or communication.

The therapeutic module system 200 of a preferred embodiment functions to serve as the internal electrical system for the therapeutic apparatus. Additionally, the therapeutic module system 200 functions to facilitate interaction between a subject and the therapeutic apparatus. The therapeutic module system 200 preferably includes a set of interaction devices. The therapeutic module system 200 may additionally include other electrical components such as a wireless communication system, processing system 300, charging or power system components, and/or any suitable electrical or computing system elements.

In one variation, the therapeutic module may be a fully integrated device contained within a singular protective casing. This single body variation of the therapeutic module system 200 may serve to make the electrical components to be easy to insert and remove from the external casing 100.

In another variation, the therapeutic module system may be a set of distinct physical elements comprised of multiple protective casing bodies. These multiple bodies may be electrical/communicatively coupled through wire or other conductive pathways. The multiple bodies may alternatively communicate wirelessly and/or self manage power. For example, a set of separately encased portions of the therapeutic module system can include an internal power system and communicate wirelessly to a base computing system. A multi body variation of the therapeutic module system 200 may serve to locally position different electrical components in strategic locations of the external casing 100. For example, a touch sensor may be placed along the back surface of a plush cat and a speaker system may be positioned near the mouth.

The interaction devices of a preferred embodiment function to as input and/or output elements used to manage an aspect of interaction with the subject. An interaction device may be an input device, an output device, or both an input and an output device. Any reasonably sized interaction device may be implemented as desired. A preferred set of interaction devices includes: sensing input subsystems that include a microphone, a haptic sensing system, and one or more biometric sensor; and output subsystems that include at least a speaker device and a haptic feedback system. The interaction devices may additionally include other subsystems such as a simulated breathing system. Other preferred interaction devices include an inertial measurement unit, biometric sensors, and location sensors. The biometric sensors can include sensing systems for measuring heart rate and other heart/pulse related signals, breathing/respiratory signals, and/or body temperature. Other sensing systems for blood chemistry analysis, mental state analysis, heart activity (e.g., via an electrocardiogram), and/or other forms biometric sensing can additionally or alternatively be used.

One or more of the interaction devices and/or other system components may be integrated together within an encased body of the therapeutic module system 200. In one preferred variation, at least a subset of the interaction devices are modular, in that the input/output devices may be added or removed (i.e. removable) from the therapeutic apparatus and oriented within the therapeutic apparatus as desired. Interaction devices may be removable individually, removable as groups of multiple devices, and/or removable as a package of all interaction devices as discussed above. In some preferred variations, a group of "base set" internal components (that include some and/or all interaction devices) is removable as a single group, while other interaction devices are removable individually and/or as distinct groups.

Some and/or all interaction devices are preferably encased within a protective body of the therapeutic module system 200 within the external casing 100. The protective body can be a rigid body such as a plastic casing. In another variation, the protective body could be, or include, a flexible body. In one variation, the base set is encased in the protective body while other interaction devices may, or may not, be inside the protective body as desired.

Some and/or all interaction devices may be device inputs. A device input is preferably a subsystem that includes at least one sensor and functions to collect input data. Examples of device inputs can include haptic sensing systems from the haptic system (e.g. touch sensors), the inertial measurement unit, and/or microphone(s). The set of device inputs could additionally or alternatively include other sensors, such as a camera, a light sensor, location/positioning sensing module, biometric sensors, and other similar sensors. A photonic sensor could include a sensing system for detecting visible and/or infrared light and may be used for detecting various aspects about the subject including lighting conditions in the environment, proximity detection, presence detection, activity detection, and the like.

Some and/or all interaction devices may be device outputs. The device outputs are preferably designed to simulate various forms of expression by the therapeutic apparatus. These expressions generally imitate various forms of animal actions (e.g., purring), but could be any suitable form of output (e.g., playing music). These forms of expression can preferably serve a therapeutic purpose (e.g. simulating a cat purring may be utilized to calm a user). An exemplary set of output devices could include, a heartbeat module, a respiratory system, haptic feedback systems from the haptic system (e.g. vibrational tool to simulate animal purring), and/or a vocalization system. The various device outputs can use different elements such as vibrational or tactile feedback mechanism (e.g. a vibrational motor) and audio speakers. In some variations, one or more forms of feedback can be synchronized to sensed biometric signals. For example, simulated purring or a simulated heartbeat output by the system may be synchronized with sensed heart rate and/or respiratory rate of the subject. Such synchronization can function to calm the subject. Other forms of outputs can include lighting elements, a display, actuated components, and/or other suitable electronically controlled outputs. More specifically, the processing system 300 can be configured to synchronize an output pattern of at least one of the output systems to the biometric data and then, over a time window, change the pattern to a target biometric pattern. For example, after synchronizing simulated breathing or purring sounds to the breathing pattern and/or heart rate of the subject, the rates of the output signals can be incrementally changed (e.g., reduced or sped up) to a more desired rate.

In one variation, one of the interaction devices is a microphone. A microphone functions as an audio sensor that detects audio and/or collects audio data. The microphone is preferably used to detect when a user is audibly interacting with the system. In some variations, this may be basic interpretation of audio magnitude (e.g. detect if the user is screaming or whispering or asking for help). In other variations, the microphone can include interpretation of the audio through audio classification (e.g., detecting speech versus other sounds), speech to text, speaker detection (e.g., detecting when the user is speaking or distinguishing between multiple users), sentiment analysis (e.g., classifying the tone of speech), and/or other forms of audio interpretation. In one operating mode, the microphone may be used to detect distressed communication and/or speech. For example, the microphone and an audio processing module could be used for detecting calls for help and then alerting or communicating with an appropriate destination like a caregiver or an emergency call center. In another example, the microphone may detect elevated volumes in speech, which may be associated with agitation for which the control system may be configured to initialize a calming operation mode.

In another variation, one of the interaction devices is a speaker system. The speaker system functions to play audio and/or provide aural stimulation from the therapeutic apparatus. Aural stimulation may be to simulate living behavior and/or to provide therapeutic aid to the user. Other types of aural feedback (e.g. communication, entertainment, music) may also be implemented as desired. The speaker system preferably includes at least one speaker device. Examples of simulated living behavior sounds may include: cat meows, breathing sounds, and barking.

The speaker system may function in complement with other interaction devices to provide a better "realistic" user experience. In some variations the speaker system may function with the haptic system to better simulate pet behavior. Examples include: the speaker system may be part of the purr-system and/or the breathing system and provide soft purring sounds and/or breathing noises in complement to motion provided by the haptic system.

The speaker system may additionally enable communication with the user. For example, in a clinic environment, the speaker system may enable an administrator, clinic caregiver, or other user to speak to a user/patient through the speaker system.

The speaker system may additionally provide therapeutic aid beyond the scope of a simulated living device (e.g. a therapy pet). For therapeutic purposes the speaker may play soothing sounds, relaxing music, repeat motivational mantras, or provide other types of therapeutic aural stimulation.

In another variation, one of the interaction devices comprises a set of biometric sensors. Biometric sensors function to collect various biometric signals associated with the patient such as heart beat sensor, respiratory rate sensing, body temperature sensor, and the like. Examples of biometric sensors include: a heart rate monitor, respiratory monitor, and a temperature monitor. Additionally or alternatively, the system may interface with a set of remote biometric sensors where biometric data of one or more user is communicated wirelessly.

In one variation, the set of biometric sensors includes an infrared (IR) emitter and detector. The IR emitter and detector functions as a heart rate monitor. The IR emitter and detector are used to measure heart rate by detecting the change in blood flow in the finger of the patient. As blood is pumped through veins, the finger becomes slightly opaque, resulting in a change in reflected infrared intensity. The IR detector will respond by changing the voltage at its output. Using a peak-finding algorithm, the periodicity of the peaks can be measured and translated into heartbeats per minute, BPM. The IR emitter and detector are preferably placed in the paws of the plush body, but may be alternatively situated in other locations on, or within, the therapeutic apparatus. Additionally or alternatively, a heart rate sensor may include a red or green LED illumination and sensing system to measure heart rate using a process of photoplethysmography where a portion of skin is illuminated and light reflected or transmitted is measured. Other heart rate sensing systems may additionally or alternatively be used.

In one variation, the heart rate monitor may further include a force sensor to accompany the IR emitter and detector. The force sensor functions to assist in power saving functionality with the IR emitter and detector by selectively activating the IR emitter and detector. The force sensor may activate the IR emitter and detector at some threshold when it detects an amount of force or activity level. In one preferred implementation, the force sensor works by acting as a potentiometer in a voltage divider; the greater the force it detects, the lower its resistance is.

In another variation, the biometric sensors further include an IR temperature sensor. The IR temperature sensor functions to measure the user body temperature. The IR temperature sensor may use IR sensitive thermopile detector chip to detect the ambient temperature around the sensor. The IR beam of the IR temperature sensor may be used in conjunction with a pre-programmed emissivity coefficient that compares how well a detected object emits infrared radiation in comparison to a theoretical blackbody that the sensor approximates. In one preferred example, the IR thermometer sensor is placed in the nose of the plush body. In preferred implementations, the IR thermometer is accurate within the range of ±1 C of the patient temperature.

In another variation, the biometric sensors further use a digital microphone to measure the breathing rate of a user. Other suitable respiratory sensing systems and approaches may similarly measure respiratory rate.

In some variations, the interaction devices include an inertial measurement unit (IMU). The inertial measurement unit functions to detect motion. The inertial measurement unit can include sensors like an accelerometer, digital gyroscope, and/or a magnetometer. Other sensors such as a tilt sensor and the like could alternatively be used to detect motion and/or orientation.

One preferred input/output device is a haptic system. The haptic system can include a haptic sensing system (i.e., haptic receiver) and/or at least one haptic feedback system (i.e., a haptic transmitter/output system), although in simple implementations, the haptic system may have only a receiver or transmitter. The haptic system functions to receive tactile input from the haptic sensing system(s) and provide tactile stimulation through the haptic feedback system(s) (e.g. vibrating motion to provide tactile simulation to a user of a cat purring).

The haptic sensing system functions to receive tactile input; that is, detect the user physical interaction with the therapeutic apparatus. The system may have at least one haptic sensing system, however the system preferably includes multiple haptic sensing systems. As a set, the haptic sensing systems preferably detect when, where on the therapeutic apparatus, and the type of physical interaction that occurs. Examples of types of tactile stimulation by the user onto the therapeutic apparatus include: petting, patting, snuggling, holding, squeezing, and hitting.

Wherein multiple haptic sensing systems are implemented, the haptic sensing systems may be of the same or different types. Two preferable types of haptic sensing systems include a touch sensor and a proximity sensor. Examples of other additional haptic sensing systems include: capacitive touch sensor, pressure sensor, bend sensor, and force-sensitive sensor. The IMU may additionally be used in conjunction with or in place of the haptic sensing system in some variations. Any additional or alternative haptic sensor may be implemented as desired. In one variation, the set of sensors can be an array of a uniform type of sensor. In another variation, the set of sensors could be a set of various types of touch sensors. Different forms of interaction could be detected through detection of different patterns of sensor data from the array of sensors. Historical patterns of interaction such as how an individual touched or interacted with the system in the past could additionally be applied in analyzing or characterizing touch interactions. For example, the system could dynamically generate a customized characterization of comforting touch interaction and agitated touch interaction. Different users may handle the system in more gentle or rougher ways (e.g., due to physical ability), and such dynamic characterization can be used to appropriately interpret user interactions, both to distinguish individual user interactions and to identify general user interaction trends.

Multiple regions or zones can be configured, using a haptic sensing system such that the system can detect the location of a physical interaction. Additionally, detecting the location, and the change of location, of tactile input could be used to determine more information about types of tactile interactions (e.g. the direction the user is petting the therapeutic apparatus).

In one preferred implementation, the haptic sensing system can include conductive material, such as velostat, that is integrated into sections of the external casing 100 or integrated alongside other internal devices. The conductive material changes resistance when deformed thus enabling detection of touch or physical interaction. The conductive material could alternatively be integrated within the plush body. In another variation, conductive thread can be integrated into the plush body outer coating and used in various forms of conductive or capacitive sensing. The conductive thread can be stitched, sewn, or otherwise integrated into the plush body outer coating. In another variation, conductive thread or elements may be integrated into the fur fiber/filaments.

Conductive thread may be integrated into the plush body in a patterned arrangement to customize the haptic sensing to a particular form of interaction. For example, a series of distinct bands (i.e., regions) of conductive stitching can be patterned down the back of the outer casing 100, which functions to detect petting up and down along the back. A band can be one or more conductive trace or surface defined through conductive thread or other conductive material that is conductively coupled together. Patterning a band preferably includes sewing one or more thread in a pattern for sensing touch contact. The different bands are preferably conductively isolated from adjacent bands. In another variation, a matrix of different conductively coupled regions could be can be patterned across all or a portion of the outer casing 100 so that touch input could be detected across a surface of the outer casing 100. In yet another variation, there can be distinct regions in different zones of outer regions to sense contact from a high level perspective (e.g., head contact, back contact, belly contact, foot contact, etc.) The conductive thread is preferably conductively coupled to touch sensing circuitry configured to measure electrical signals and interpret haptic input.

Haptic feedback systems of the haptic system function to simulate appropriately desired "living" behavior in the therapeutic apparatus and to provide therapeutic aid to the user. The haptic feedback system is preferably enabled to emulate and respond in an approximation to the living organism that the external casing 100 resembles. Examples of simulated living behavior include: animal breathing, an animal hart beat, cat purring. Simulated living behavior may be also used in therapeutic aid (e.g. gentle animal purring to calm the user).

The haptic feedback systems include a vibrational motor as part of a heartbeat module. The heartbeat module functions to simulate a heartbeat. The heartbeat module preferably uses a vibrational feedback mechanism to generate a periodic output of a simulated heartbeat. The speed and intensity/volume of the heartbeat is preferably controllable. In one preferred implementation, states of user agitation could be detected using a microphone and/or accelerometer. Elevated states of agitation could be responded to by engaging the heartbeat module to soothe or calm the patient. In one variation, this can include increasing the intensity or amplitude of the heartbeat so that it is more easily sensed by the patient. The intensity can be decreased as the patient is calmed. In another variation, the heartbeat frequency can be set to a first high rate. In implementations where the heartbeat of the user can be sensed, the high rate could be substantially matched to that of the patient. Then the frequency can be decreased overtime to facilitate returning the user to a calmer state.

The haptic feedback systems may include a vibrational motor as part of a purr-system. The purr-system may additionally include or operate in coordination with the speaker system. The vibrational motor may function to simulate animal purring through vibrational motion while the speaker system makes soft purring sounds. In one implementation, purr-system initiates purring in response to detected petting, snuggling, or similar forms of contact. The rate and intensity of the purring is preferably controllable. In another implementation the purr-system initiates purring in response to an agitated user, similarly as described for the heartbeat module, wherein purring may aid to calm down the agitated user.

The haptic feedback systems may include actuating motors as part of a breathing system. The breathing system or more specifically a respiratory simulation mechanism, may additionally include or operate in coordination with the speaker system. The actuating motors may function to simulate animal breathing through expansion and contraction of the therapeutic apparatus in conjunction with breathing sounds played by the speaker system. The speed and intensity of the breathing is preferably controllable. The breathing system could be controlled in a manner similar to the heart beat module and used to assist a patient in transitioning from an agitated state to a calm state. The breathing and/or heart rate output of the interaction devices may be controlled to synchronize with the subject or in some cases lead the subject to a more desired pattern of breathing and/or heart rate. For example, if the sensed breathing and/or heart rate of the subject is elevated, the interaction devices may set their output to be near but less than the subjects, and then steadily decrease as the subjects respiratory rate and/or heart rate decreases.

A vibrational haptic system can similarly be used in different modes to simulate breathing, purring, a heartbeat, and/or any other haptic output mode.

Other interaction modular input/output devices may be implemented as desired. For example, GPS location could be detected and provided by a communicatively coupled computing device like a smart phone.

Preferably the therapeutic module system 200 includes a wireless communication system. The wireless communication system enables communication between the modular input/devices within the therapeutic apparatus and external related systems (e.g. remote portions of the processing system 300 and external clients maintained by an administrator, remote cloud system). The wireless communication system may be based on any desired type of wireless technology, for examples: Wi-Fi, Bluetooth, cellular and/or any combination of these or other wireless technologies. In some preferred variations, the implemented wireless technology is Bluetooth. In another preferred variation, the implemented wireless technology is Wi-Fi such that the wireless communication system communicates to a local Wi-Fi network.

The processing system 300 of a preferred embodiment functions to receive input data from device inputs of the simulated living device and process the input data. That is, the processing system 300 may function to facilitate classification, interpretation, translation, and/or other forms of processing of monitored input data. Preferably the processing system 300 is configured to assess the state of a subject through one or more sensing inputs of the interaction devices and then control the output systems of the interaction devices in response to the sensing inputs. More specifically, the processing system 300 is configured to collect interaction signals of the subject, interpret the interaction signals, and control the output systems. In one preferred mode, configuration to assess the state comprises configuration to characterize an agitation state of the subject; and then to initiate an agitation mode to mitigate agitation of the subject.

Various control flows may be implemented in determining operation of the therapeutic module system. The processing system 300 may coordinate sensing of inputs, communication with external compute and data resources, and control of outputs. This may include tracking time and location, detecting petting or talking to animal, sensing biometric signals, assessing level of distress or agitation, controlling simulated outputs (like purr simulation, heartbeat simulation, or respiratory simulation), and synchronizing data.

In one example, audio data could be classified as speech, undergo a speech to text conversion, undergo sentiment analysis (e.g. on the content of speech and/or the manner in which someone is speaking) and/or be processed in any suitable manner. Multiple types of input data could additionally be used in combination to determine the current context. In one implementation, the system processes input data to monitor verbal communication between the therapeutic apparatus and the user.

The processing system 300 may be wholly encased within the therapeutic apparatus, but is preferably an external component of the system that receives input data through the wireless communication system. In some variations the processing system 300 may have modular subcomponents within the therapeutic apparatus to process some input data while other portions of data processing happens in a communicatively coupled remote computing resource (e.g., a remote client or a cloud platform). In some variations the processing system 300 is a processing unit of the therapeutic module system 200. In some variations, the processing system 300 may be a cloud based processor.

Through the processing system 300, the system may identify and/or learn user trends. For example, over some period of utilization, a distinct user may be identified and distinguished from other users. A user may be identified through their voice pattern, speech pattern, behavior in handling a therapeutic apparatus (e.g. how rough or gently the user is), behavioral patterns (e.g. a user is agitated at a particular time of day, or the user always arrives at a certain time of day), and/or other suitable patterns.

Identification of a user and identification of user trends may further enable user specific interaction with the therapeutic apparatus. For example, through repeated interaction with the system, the processing system 300 may learn that a user/patient typically becomes agitated in the evening. The system may then take preemptive measures to help calm the user.

The processing system 300 can preferably include a number of control modules configured to control the outputs in concert with inputs and assessed state of one or more subjects. Heuristic-based rules may be set to define patterns of interaction that then are used to trigger the control module to initiate a particular control mode. Additionally or alternatively, machine learning or other forms of personalization may be applied such that the form of a directed control mode is augmented based on previously measured responses to the control mode. In this way, the system may learn how to control the therapeutic apparatus. This learning may be applied across multiple different users. Alternatively, the learning could be at least partially customized to a particular user.

The control module of a preferred embodiment functions to control the operation of the therapeutic apparatus. The control module preferably receives interpreted data from the processing system 300, and in response, sets the operating state of one or more outputs. The control module may configuration that is part of the processing system 300. The control module preferably has a number of operating modes, such as comfort mode, agitation mode, maintenance mode, monitor mode, interaction mode, and/or other suitable types of operating modes. Some modes may be default or background modes that are substantially active during other operating modes. The various operating modes may alternatively be selectively controlled by an external administrator/caregiver as desired.

An interaction mode is preferably the default mode of interaction. In the interaction mode, the therapeutic apparatus may simulate typically expected "animal" behavior and response to the user. For example, the purr-system may start purring when the user pets or holds the therapeutic apparatus.

An agitation mode is preferably selectively engaged when elevated states of agitation are detected from the user. The heartbeat module, respiratory system, vocalization system, purr-system, and/or other outputs are preferably activated to promote a return to a calm state. In some implementations, the therapeutic apparatus may simulate a calm heartbeat through the heartbeat module to attempt to calm the user. In one variation, the processing system 300 when in an agitation mode selects from controlling the outputs from a set of output modes. The various output modes can include simulated purring, simulated heartbeat, and simulated breathing. In a variation that applies learning, the type of output mode can be altered based on a subject's history of response to the various types of output modes. Accordingly, the selection processing system 300 may be configured to alter selection of the output modes based on detected inputs from the subject in response to previous output modes. In one implementation, the processing system 300 may first match the user heartbeat with the heartbeat module and match the user breathing rate with the respiratory system, and then attempt to calm the user by gradually slowing down the heartbeat module and respiratory system.

A comfort mode may be a background mode that promotes active engagement with the therapeutic apparatus. The comfort mode may be utilized if the user appears to be very disengaged or non-interactive for some period of time. The comfort mode preferably encourages physical contact and/or vocal engagement with the therapeutic apparatus. This mode comprises detecting petting of and/or talking to the simulated living. During active engagement, purring and/or vocalization can be activated to reinforce or signal the positive aspects of this engagement. In another variation, the amount of engagement and frequency can be tracked. If a user isn't satisfying some threshold of amount of engagement, the system can activate various components to signal to the patient and/or the caregiver the need for more engagement. For example, the device can detect when it has been left unattended and make an animal sound such as a bark or meow to remind the user of its presence in an attempt for them to re-engage with it.

A monitor mode may be another type of background mode wherein the therapeutic apparatus monitors the behavior of a user possibly without providing external output. In some instances external output may be initiated while data is still collected for monitoring. In the monitor mode, the therapeutic apparatus may observe, record, and process the activity of the user. The system will preferably include an administrator system, which could be a client device, a network accessible application/web dashboard, and/or any suitable type of user interface for which a second user or caregiver could monitor. The administrator system may be used for presenting historical records (agitation states, periods of rest, engagement levels with the apparatus, etc.). In some variations, the therapeutic apparatus may monitor one user, while simultaneously engaging with another user. For example, one patient may be playing and interacting with the therapeutic apparatus while the therapeutic apparatus is additionally monitoring another patient.

In the case of verbal engagement, the system can comprise detecting and monitoring vocal engagement by detecting a patient addressing an animal by saying its name, detecting a patient performing some class of communication (e.g., baby talk), detecting object directed communication using a camera for facial recognition or attention, and the like. A vocalization module could generate various sounds in response to the patient. In some cases, these sounds can be synthesized or selected in response to the nature of communication by the user. Through learning, these vocalizations may additionally change to suit the user.

A maintenance mode preferably serves to signal to an administrator/caregiver various aspects related to the care of the system. A maintenance mode could signal when the system should be recharged or needs some other form of maintenance. Another maintenance mode can preferably regulate the power. The system can activate various forms of power saving modes such as a sleep mode where a subset of the inputs and/or outputs may be deactivated or operated in a sleep mode. The system additionally enters a standby mode during times of inactivity. For example, the system could detect when the system is held by the patient but the patient has fallen asleep or becomes disengaged such as when the system by detecting touch contact but no movement. Sounds could be deactivated to avoid disrupting the patient.

The control module may additionally and/or alternatively function under manual control of an administrator/caregiver. The caregiver may modify a functioning operating mode, or implement a completely different behavior. For example, if a treatment facility knows that a user/patient is hard of hearing, the caregiver may modify the operation modes such that all therapeutic apparatus vocalizations directed at the hard of hearing patient are louder.

An optional management application functions to enable caregivers and others remote entities access into usage, settings, and/or other aspects of the system. The management application can communicate directly with the control module of the therapeutic apparatus. Alternatively, the control module can communicate with a remote server that then communicates with a management application. The management application can be a web-based application, native application, a dedicated monitoring device, and/or any suitable type of application. When used within a hospital or caregiver scenario, multiple instances of a system can be connected to a single account enabling a caregiver to monitor multiple patients or subjects within the management application.

Particularly as part of a caregiver facility, the system may further comprise of multiple therapeutic apparatuses. Each therapeutic apparatus may function independently with a given user, multiple therapeutic apparatuses may function with a single user, a single therapeutic apparatus may function with multiple users, or any desired combination of interactions may be implemented. As a group, multiple therapeutic apparatuses may function identically or in a complimentary fashion. For example, for an agitated patient: the therapeutic apparatus that the user is holding may start purring, while and another proximal therapeutic apparatus may start playing music or making soft animal noises (e.g. barking, meowing). A set of therapeutic apparatuses may be configured to communicate data to a central resource (e.g., a base station or client device, a cloud platform, etc.), and a change in one or more therapeutic apparatuses may be made responsive to data of one or more therapeutic apparatuses. In another example of coordinated operation, a first apparatus may detect an agitated subject, and then this may be used to alter the threshold for engaging an agitation mode in other nearby apparatuses. The threshold may in some variations be lowered based in part on proximity to the agitated subject. In another variation, the threshold or condition for triggering the agitation mode is not changed but instead the agitation mode is automatically engaged in response to detection of a nearby subject in state of agitation. This can be particularly useful in an assisted care situation where heightened states of agitation typically trigger agitation in nearby users. Multiple therapeutic apparatuses may be controlled from the same external management application or from a distinct external management application as desired.

The system of a preferred embodiment includes a charging system 400. In a preferred implementation, a wireless charging power system is used to wirelessly charge a battery. The battery and the battery encasement are preferably modular and thus removable from the therapeutic apparatus. A wireless charger base station preferably wirelessly charges a wireless charger receiver integrated into the battery encasement. In one implementation, the wireless charger base station is integrated into a pet bed, carrier or other holder for the therapeutic apparatus. The battery casement in this implementation is preferably positioned along the base or bottom of the plush body and aligned for better wireless charging. LEDs, displays on phone application, or other forms of output can be used to signal to the patient or caregiver when the system needs charging, is charging, and/or has been charged.

3. Method for Therapeutic Aid Through a Therapeutic Apparatus

As shown in FIG. 3, a method for therapeutically aiding a user via a therapeutic apparatus includes: collecting patient interaction signals S110, interpreting the interaction signals S120, and controlling output of the therapeutic apparatus in response to the interpreted interaction signals S130. The method is preferably implemented by a system substantially similar to the one described above, but any suitable system may alternatively be used. The method is preferably used to promote various aspects of a therapeutic apparatus, or multiple therapeutic apparatuses, that function in a therapeutic manner with a user and/or patient. In particular, the method can define a set of operational processes that can promote physical engagement, positively affect the mental or physical state of a patient, and/or signal that additional care for the patient is required.

Block S110, which includes collecting patient interaction signals functions to detect various inputs from a patient or multiple patients. Collecting patient interaction signals S110 can include recording audio, measuring kinematic activity and/or orientation (e.g., via an accelerometer, gyroscope, tilt sensor, etc.), detecting touch contact, detecting patient presence, sensing biometric signals, collecting visual data, machine olfaction, and the like.

Block S120, which includes interpreting the interaction signals S120, functions to analyze and detect various conditions in the therapeutic signals. This can be used in detecting different states of interaction with the therapeutic apparatus or with multiple therapeutic apparatuses. Interpreting the interaction signals can include classifying touch input, sound input, general behavior input, and any/or additional type of relevant patient input. Touch input may be classified as petting, patting, hitting, holding, squeezing, and/or other suitable types of contact. Sound input may include audio classification (e.g., detecting speech vs. other sounds), speech to text, speaker detection and identification (e.g., detecting when the patient is speaking, sentiment analysis (e.g., classifying the tone of speech), and/or other forms of audio interpretation. Interpreting interaction signals can use heuristic-based analysis by looking for discrete conditions. Machine learning or other forms of algorithmic analysis are used to interpret collected data.

Block S130, which includes controlling the output of the therapeutic apparatus functions in simulating "real life" functional response of the therapeutic apparatus. Controlling output of the therapeutic apparatus S130 can include controlling one or more types of outputs such as a heartbeat module, a respiratory module, a vocalization system, a low vibratory sound or purr system, a vibrational or tactile feedback mechanism (e.g., a vibrational motor), an audio speaker, a lighting element, a display, actuated components, and/or other suitable electronically controlled outputs.

As discussed, controlling the output of the therapeutic apparatus S130 may be used to encourage physical engagement with a therapeutic apparatus. This may be used in rewarding engagement with the therapeutic apparatus. In one variation detecting audio above a certain threshold can be interpreted as audio communication and can trigger some reinforcing reward action like triggering a vocalization, purring, and the like. In another variation, an output response can be dynamically generated based on the interpretation of therapeutic signals, which can function to create variety in the patient's interactions and to appropriately respond to different contexts. For example, different animal sounds could be synthesized according to the nature of verbal communication with the system. For example, if the sentiment of communication by a patient is determined to be sad, the therapeutic electronic device could make comforting animal sounds that positively affect the perceived patient state-of-being.

In another variation, encouraging physical engagement with a therapeutic apparatus may be used to remind a patient to become engaged. Engagement with the therapeutic apparatus can be tracked and when engagement goals are not satisfied, the device could trigger a signal like a sound. For example, the therapeutic apparatus could make a barking or meowing sound. In one exemplary scenario, these reminders may be directed to reminding a patient to interact or engage with the therapeutic apparatus. In other exemplary scenario, reminders could be produced to remind patients to exercise, take medication, eat or drink, rest, or perform other suitable or scheduled activities.

Controlling the output of the therapeutic apparatus S130 could additionally or alternatively be applied to soothing or augmenting the state of the patient through one or more controlling one or more outputs. This preferably involves detecting a negative state and activating various outputs that can promote a positive state. For example, detecting agitation through loud sounds or rough treatment of the interactive therapeutic device can be responded to by activating the heartbeat module. This may include amplifying the heartbeat signal temporarily, matching the heartbeat signal to that of the patient, simulating the heartbeat transitioning from a fast rate to a slow, calm rate, or any suitable augmentation of the heartbeat signal. In a related variation, controlling the output could be applied to soothing a patient during periods of rest. The method could detect sleep agitation and trigger various outputs to promote a return to rest or sleep. For example, the method could automatically play a soothing sound when the system detects the patient wakes from sleep at night.

Controlling the output of the therapeutic apparatus S130 could additionally or alternatively be applied in response to a data collected from a second therapeutic apparatus. In this variation, two or more therapeutic apparatuses that are used in proximity to each other can coordinate operation. As initial optional steps, the method can include each of the therapeutic apparatuses detecting location and identifying apparatuses in near proximity. Detecting location may use various geolocation sensing approaches (e.g., GPS), but may alternatively use general location sensing techniques such as detecting an RF beacon, Wi-Fi access points, or other general location indicators. Other suitable location sensing techniques may alternatively be used. Near proximity could be defined in any suitable manner. Alternatively, the method may include registering two or more apparatuses as paired. Using preset configuration to pair apparatuses may be used when it is generally known that the apparatuses and their subjects will be in close proximity.

In coordinating operation, the method preferably includes in response to processed sensed input of a first apparatus, augmenting the output of at least a second apparatus. In one variation, augmenting the output may include augmenting the output partially proportional to proximity.

Controlling the output of the therapeutic apparatus S130 could additionally or alternatively be applied to signaling needed care for the device. This preferably includes activating an output when the batteries require charging. For example, the interactive therapeutic device could produce a particular barking sound when it should be charged. In another variation, the various operating modes could altered based on the usage of the therapeutic animal to conserve battery, prevent the device from annoying a patient, avoid disrupting a patient while they are sleeping.

4. Method of Manufacturing and Caring for a Therapeutic Responsive Object

A method for manufacturing plush body animals preferably includes the treatment of the fur coating with sanitation processing, which functions to give a therapeutic interactive aid device enhanced hygienic properties, such as antimicrobial and/or antifungal properties. An interactive aid device is expected to have extended physical contact with the patients during the day and over long durations, wherein many facilities also cannot afford or have facility to support frequent washing and/or other care of a plush body. The method for treatment of fur coating can be used with a therapeutic apparatus as described above.

The method can mitigate or remove issues with hygiene for interactive aid devices such as the one described above or any suitable device with a plush fur body. The sanitation processing of the fur coating can enhance the usability of the interactive aid device by minimizing or even eliminating the need to clean the plush body.

A method for a sanitation processing of a therapeutic plush body fur coating can includes creating an antimicrobial solution and applying the antimicrobial solution through a submersion process. The antimicrobial solution can be a variety of antimicrobial solutions. Three preferred variations include: a zinc pyrithione and thiabendazole solution, a zinc pyrithione solution, and a silver chloride and polymer dispersion two part solution treatment. Other variations include a chitosan solution and a laundry antimicrobial solution. Different fur textures may receive varying treatments.

As shown in FIG. 4, a method for implementing a zinc pyrithione and thiabendazole solution and a zinc pyrithione solution for a sanitation processing of a plush body fur coating preferably include: preparing an antimicrobial solution pad bath S210 at appropriate concentration of antimicrobial solution, running the fur coating through the pad bath S220, and drying the fur coating S230.

Block S210, which includes preparing a pad bath, functions to create the antimicrobial bath that will treat the plush body fur coating. The concentration of a zinc pyrithione and thiabendazole solution is preferably 0.2-0.7% by weight of the plush body fur coating for the zinc pyrithione and thiabendazole solution implementation, and the concentration of a zinc pyrithione solution is preferably 0.14-0.7% by weight of the plush body fur coating for a zinc pyrithione solution implementation. The weight of the plush body fur coating may be determined by an experimental pick-up rate.

Block S220, which includes running the fur coating through the pad bath, functions in treating the plush body fur coating with the antimicrobial treatment. The pad bath is preferably constantly agitated during S120.

Block S230, which includes drying the fur coating, functions in finishing the microbial treatment. In preferred variations, the plush body fur coating is dried in an autoclave at 150-180 C for at least 45 seconds.

As shown in FIG. 5, a method for implementing a zinc pyrithione solution, and a silver chloride and polymer dispersion two part solution treatment for sanitation processing of a plush body fur coating preferably includes: heating the silver chloride S310, preparing an antimicrobial bath at appropriate concentration of antimicrobial solution S320, creating an antimicrobial pad bath solution S330, treating the fur coating with the pad bath S340, and curing fur coating S350.

Block S310, which includes heating the silver chloride, functions to prep the silver chloride. The silver chloride is preferably lightly agitated during the heating. In preferred variations, the silver chloride is heated to 25-30 C.

Block S320, which includes preparing an antimicrobial solution, functions in creating the zinc pyrithione solution, and a silver chloride and polymer dispersion two part solution treatment mixture. Preparing the antimicrobial solution S320 preferably includes slowly mixing the heated silver chloride with the polymer dispersion. In preferred implementations, the mixture is 6-10% silver chloride to 80-94% polymer dispersion.

Block S330, which includes creating an antimicrobial pad bath solution, functions in creating the zinc pyrithione solution, and a silver chloride and polymer dispersion two part solution treatment pad bath. Creating an antimicrobial pad bath solution S330 preferably includes slowly mixing the silver chloride, polymer dispersion mixture with the pad bath with minimal light exposure.

Block S340, which includes treating the fur coating, functions in applying a zinc pyrithione solution, and a silver chloride and polymer dispersion two part solution treatment solution to the fur coating. In preferably variations, the fur coating is treated by 2.0-2.5% a zinc pyrithione solution, and a silver chloride and polymer dispersion two part solution treatment pad bath by weight.

Block S350, which includes curing the fur coating, functions in finishing the zinc pyrithione solution, and a silver chloride and polymer dispersion two part solution treatment antimicrobial treatment. Curing the fur coating S350 preferably occurs at 150 C for a period of greater than 45 seconds.

The systems and methods of the embodiments can be embodied and/or implemented at least in part as a machine configured to receive a computer-readable medium storing computer-readable instructions. The instructions when executed by one or more processors of a machine cause the machine to perform operations such as those described herein. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMS, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

I claim:

1. A therapeutic system comprising:
    an external casing of a first therapeutic apparatus, wherein the external casing comprises of a plush body, the external casing comprising at least one compartment;
    a therapeutic module system that comprises of a set of interaction devices and a wireless communication system, wherein the therapeutic module system is removably oriented into the at least one compartment;
    wherein the set of interaction devices comprises of:
        sensing inputs that comprise of at least a microphone device and a haptic sensing system, and
        output systems that comprise of at least a speaker device and a haptic feedback system, wherein the haptic feedback system comprises at least a respiratory simulation mechanism configured to expand and contract a surface of the external casing; and
    a processing system that comprises configuration to assess a state of a subject through the sensing inputs and control the output systems in response to the sensing inputs.

2. The system of claim 1, wherein the configuration to assess the state of the subject characterizes an agitation state of the subject; and wherein control of the output systems initiates an agitation response mode to mitigate agitation of the subject.

3. The system of claim 2, wherein the processing system when in an agitation mode selects from controlling the outputs from a set of output modes that comprise of simulated purring, simulated heartbeat, and simulated breathing; and wherein selection by the processing system is configured to alter selection of the output modes based on detected inputs from the subject in response to previous output modes.

4. The system of claim 1, wherein configuration to assess the state of the subject through the sensing inputs comprises configuration to collect interaction signals of the subject and interpret the interaction signals.

5. The system of claim 1, the processing system comprising of a monitor mode; wherein when in the monitor mode, the therapeutic module system passively collects input data of the subject.

6. They system of claim 5, further comprising an administrator system, wherein the input data collected during the monitor mode is wireless communicated to the administrator system through the wireless communication system.

7. The system of claim 1, wherein the plush body is lined with synthetic fur.

8. The system of claim 7, wherein the fur is antimicrobial treated fur.

9. The system of claim 7, wherein the fur is anti-fungal treated fur.

10. The system of claim 1, wherein the haptic sensing system is configured to monitor location of tactile input and type of tactile input on the therapeutic apparatus.

11. The system of claim 1, wherein the haptic feedback system comprises of a set of distinct haptic output regions oriented at different locations of the external casing and controllable by the processing system.

12. The system of claim 1, wherein the processing system is further configured to control a second therapeutic module system based in part on sensed inputs of the first therapeutic module system.

13. The system of claim 1, wherein the haptic feedback system comprises of a vibrational motor system; wherein the processing system is configured to control the vibrational motor system in at least a purring simulation mode and a heartbeat mode.

14. The system of claim 1, wherein the set of interaction devices further comprise a set of biometric sensors configured to monitor biometric data of a user within proximity of the therapeutic apparatus.

15. The system of claim 14, wherein the set of biometric sensors comprise of a heart rate monitor.

16. The system of claim 14, wherein the set of biometric sensors comprise of a respiratory monitor.

17. The system of claim 14, wherein the set of biometric sensors comprise of a temperature monitor.

18. The system of claim 1, wherein the processing system is configured to synchronize an output pattern of at least one of the output systems to the biometric data and then, over a time window, change the pattern to a target biometric pattern.

19. The system of claim 1, further comprising a second external casing of a second therapeutic apparatus containing a second therapeutic module system; wherein the processing system comprises a remote computing system, and the remote computing system is configured to coordinate control of the first apparatus and the second apparatus.

20. A therapeutic system comprising:
    an external casing of a first therapeutic apparatus, wherein the external casing comprises of a plush body, the external casing comprising at least one compartment;
    a therapeutic module system that comprises of a set of interaction devices and a wireless communication system, wherein the therapeutic module system is removably oriented into the at least one compartment;
    wherein the set of interaction devices comprises of:

sensing inputs that comprise of at least a microphone device and a haptic sensing system, and output systems that comprise of at least a speaker device and a haptic feedback system;

a second external casing of a second therapeutic apparatus containing a second therapeutic module system; and a processing system that comprises configuration to assess a state of a subject through the sensing inputs and control the output systems in response to the sensing inputs, wherein the processing system comprises a remote computing system, and the remote computing system is configured to coordinate control of the first therapeutic apparatus and the second therapeutic apparatus.

21. The system of claim 20, wherein the processing system is further configured to control the second therapeutic module system based in part on sensed inputs of the first therapeutic module system.

22. A therapeutic system comprising:

an external casing of a first therapeutic apparatus, wherein the external casing comprises of a plush body, the external casing comprising at least one compartment;

a therapeutic module system that comprises of a set of interaction devices and a wireless communication system, wherein the therapeutic module system is removably oriented into the at least one compartment;

wherein the set of interaction devices comprises of:

sensing inputs that comprise of at least a microphone device and a haptic sensing system, and output systems that comprise of at least a speaker device and a haptic feedback system wherein the haptic feedback system comprises a vibrational motor system; and a processing system that comprises configuration to assess a state of a subject through the sensing inputs and control the output systems in response to the sensing inputs, wherein the processing system is configured to control the vibrational motor system in at least a purring simulation mode and a heartbeat mode.

23. The system of claim 22, wherein the processing system is configured to synchronize an output pattern of at least one of the output systems to the biometric data and then, over a time window, change the pattern to a target biometric pattern.

24. A therapeutic system comprising:

an external casing of a first therapeutic apparatus, wherein the external casing comprises of a plush body, the external casing comprising at least one compartment;

a therapeutic module system that comprises of a set of interaction devices and a wireless communication system, wherein the therapeutic module system is removably oriented into the at least one compartment;

wherein the set of interaction devices comprises of:

sensing inputs that comprise of at least a microphone device and a haptic sensing system, and output systems that comprise of at least a speaker device and a haptic feedback system; and a processing system that comprises configuration to assess a state of a subject through the sensing inputs and control the output systems in response to the sensing inputs, wherein the configuration to assess the state of the subject characterizes an agitation state of the subject, wherein control of the output systems initiates an agitation response mode to mitigate agitation of the subject, and wherein the processing system when in an agitation mode selects from controlling the outputs from a set of output modes that comprise simulated purring, simulated heartbeat, and simulated breathing; and wherein selection by the processing system is configured to alter selection of the output modes based on detected inputs from the subject in response to previous output modes.

\* \* \* \* \*